United States Patent [19]

Buchecker et al.

[11] Patent Number: 5,478,497

[45] Date of Patent: Dec. 26, 1995

[54] TETRACYCLIC COMPOUNDS AND LIQUID CRYSTALLINE MIXTURES CONTAINING THEM

[75] Inventors: Richard Buchecker, Zurich; Martin Schadt, Seltisberg; Alois Villiger, Basel, all of Switzerland

[73] Assignee: Hoffmann-La Roche Inc., Nutley, N.J.

[21] Appl. No.: 383,698

[22] Filed: Feb. 1, 1995

Related U.S. Application Data

[63] Continuation of Ser. No. 203,704, Feb. 28, 1994, abandoned, which is a continuation of Ser. No. 825,464, Jan. 24, 1992, abandoned.

[30] Foreign Application Priority Data

Feb. 1, 1991 [CH] Switzerland ................ 305/91

[51] Int. Cl.⁶ ............... C09K 19/34; C09K 19/30
[52] U.S. Cl. ............. 252/299.61; 252/299.63; 570/128; 570/182; 544/242; 544/335; 546/268; 546/330; 546/346; 549/369; 549/370; 549/373
[58] Field of Search .............. 252/299.01, 299.61, 252/299.63; 570/128, 182; 544/242, 296, 334, 335; 546/268, 330, 346; 549/369, 370, 373

[56] References Cited

U.S. PATENT DOCUMENTS

| | | | |
|---|---|---|---|
| 4,814,523 | 3/1989 | Tanaka et al. | 252/299.63 |
| 4,871,470 | 10/1989 | Wachtler et al. | 252/299.63 |
| 4,882,082 | 11/1989 | Eidenschink et al. | 252/299.61 |
| 4,886,621 | 12/1989 | Sage et al. | 252/299.63 |
| 5,030,383 | 7/1991 | Scheuble et al. | 252/299.63 |
| 5,055,224 | 10/1991 | Sage et al. | 252/299.63 |
| 5,061,400 | 10/1991 | Obikawa | 252/299.63 |
| 5,171,469 | 12/1992 | Hittich et al. | 252/299.63 |
| 5,174,921 | 12/1992 | Buchecker et al. | 252/299.63 |
| 5,185,098 | 2/1993 | Buchecker et al. | 252/299.63 |
| 5,230,826 | 7/1993 | Boller et al. | 252/299.63 |

FOREIGN PATENT DOCUMENTS

| | | |
|---|---|---|
| 0099099 | 1/1984 | European Pat. Off. . |
| 0291949 | 11/1988 | European Pat. Off. . |
| 0331091 | 9/1989 | European Pat. Off. . |
| 3734116A | 10/1987 | Germany . |
| 3734116 | 10/1987 | Germany . |

OTHER PUBLICATIONS

JP0092-228A, Abstract, Derwent, 1983.

*Primary Examiner*—Philip Tucker
*Attorney, Agent, or Firm*—George M. Gould; George W. Johnston

[57] ABSTRACT

Compounds of the formula

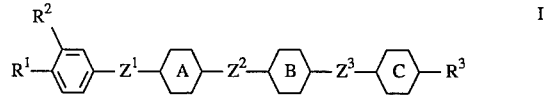

wherein rings A, B and C, $Z^1$, $Z^2$, $Z^3$, $R^1$, $R^2$ and $R^3$ are defined in the specification, their manufacture, liquid crystalline mixtures which contain such compounds and the use of these compounds for electro-optical purposes.

13 Claims, No Drawings

TETRACYCLIC COMPOUNDS AND LIQUID CRYSTALLINE MIXTURES CONTAINING THEM

This is a continuation of U.S. application Ser. No. 08/203,704, filed Feb. 28, 1994, now abandoned, which is a continuation of U.S. application Ser. No. 07/825,464, filed Jan. 24, 1992, abandoned.

SUMMARY OF THE INVENTION

The present invention comprises compounds with four rings, their manufacture, liquid crystalline mixtures which contain these compounds and the use of these compounds or mixtures for electro-optical purposes.

The present invention provides compounds of the general formula

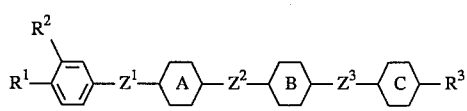

wherein
  rings A and B each independently signify trans-1,4-cyclohexylene, 1,4-phenylene, which is unsubstituted or mono- or disubstituted with halogen and/or cyano and/or methyl, pyridine-2,5-diyl or pyrimidine-2,5-diyl,
  ring C signifies trans-1,4-cyclohexylene or trans-1,3-dioxane-2,5-diyl,
  $Z^1$ an $Z^2$ each independently signify a single bond or, where linked with at least one saturated ring, also ethylene,
  $Z^3$ signifies a single bond or ethylene,
  $R^1$ signifies fluorine or chlorine,
  $R^2$ signifies hydrogen or fluorine and
  $R^3$ signifies $C_{2-12}$-1E-alkenyl, $C_{4-12}$-3E-alkenyl, $C_{5-12}$-4-alkenyl or $C_{2-12}$-alkoxyalkyl, whereby in the case of alkoxyalkyl not more than 5 methylene groups are situated between the oxygen atom and ring C,
with the provisos that
  (a) where ring B is (hetero)aromatic, ring A is not simultaneously trans-1,4-cyclohexylene,
  (b) a maximum of two trans-1,4-cyclohexylene groups each linked with a single bond are present,
  (c) a maximum of one of rings A and B is pyridine-2,5-diyl or pyrimidine-2,5-diyl and
  (d) where simultaneously $R^1$ signifies fluorine and $R^3$ signifies $C_{2-12}$-1E-alkenyl or $C_{4-12}$-3E-alkenyl, $R^2$ stands exclusively for fluorine.

BACKGROUND OF THE INVENTION

Liquid crystals are used primarily as dielectrics in indicating devices, because the optical properties of such substances can be influenced by an applied voltage. Electro-optical devices based on liquid crystals are well-known to a person skilled in the art and can be based on various effects. Examples of such devices are cells having dynamic scattering, DAP cells (deformation of aligned phases) guest/host cells, TN cells having a twisted nematic structure, STN cells ("super-twisted nematic"), SBE cells ("super-birefringence effect") and OMI cells ("optical mode interference"). The most common indicating devices are based on the Schadt-Helfrich effect and have a twisted nematic structure.

The liquid crystal materials must have good chemical and thermal stability as well as good stability towards electric fields and electromagnetic radiation. Further, the liquid crystal materials should have a low viscosity and in the cells should give short response times, low threshold potentials and a high contrast. Furthermore, at usual operating temperatures of about −30° C. to about +80° C., especially about −20° C. to about +60° C., they should have a suitable mesophase, for example, a nematic or cholesteric mesophase for the aforementioned cells. Further properties, such as the electrical conductivity, the dielectric anisotropy and the optical anisotropy must fulfil different requirements depending on the type of cell and field of application. For example, materials for cells having a twisted nematic structure should have a positive dielectric anisotropy and an electrical conductivity which is as low as possible. There has recently been a particular interest in actively addressed liquid crystal indicators, e.g., TFT applications ("thin film transistor") in television sets. The use of cyano compounds having a positive dielectric anisotropy leads, however, in such indicators mainly to an undesired high increase in current.

Since liquid crystals are usually used as mixtures of several components it is important that the components have a good miscibility with one another.

DETAILED DESCRIPTION OF THE INVENTION

The present invention provides compounds of the general formula

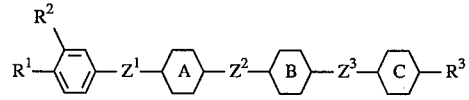

wherein
  rings A and B each independently signify trans-1,4-cyclohexylene, 1,4-phenylene, which is unsubstituted or mono- or disubstituted with halogen and/or cyano and/or methyl, pyridine-2,5-diyl or pyrimidine-2,5-diyl,
  ring C signifies trans-1,4-cyclohexylene or trans-1,3-dioxane-2,5-diyl,
  $Z^1$ an $Z^2$ each independently signify a single bond or, where linked with at least one saturated ring, also ethylene,
  $Z^3$ signifies a single bond or ethylene,
  $R^1$ signifies fluorine or chlorine,
  $R^2$ signifies hydrogen or fluorine and
  $R^3$ signifies $C_{2-12}$-1E-alkenyl, $C_{4-12}$-3E-alkenyl, $C_{5-12}$-4-alkenyl, or $C_{2-12}$-alkoxyalkyl, whereby in the case of alkoxyalkyl not more than 5 methylene groups are situated between the oxygen atom and ring C,
with the provisos that
  (a) where ring B is (hetero)aromatic, ring A is not simultaneously trans-1,4-cyclohexylene,
  (b) a maximum of two trans-1,4-cyclohexylene groups each linked with a single bond are present,
  (c) a maximum of one of rings A and B is pyridine-2,5-diyl or pyrimidine-2,5-diyl and
  (d) where simultaneously $R^1$ signifies fluorine and $R^3$ signifies $C_{2-12}$-1E-alkenyl or $C_{4-12}$-3E-alkenyl, $R^2$ stands exclusively for fluorine.

The compounds in accordance with the invention form liquid crystals having broad nematic phases and very high clearing points. At the same time, they have surprisingly short switching times, especially in indicating devices having a twisted nematic structure. They have a low viscosity and a good solubility in usual liquid crystal materials. In particular, they increase strongly the clearing point of liquid crystal mixtures and accordingly improve the nematic mesophase without simultaneously increasing the threshold potential and unduly lengthening the switching times.

The compounds in accordance with the invention are especially suitable as components of nematic and cholesteric mixtures and, by virtue of their good miscibility with one another and with known liquid crystal materials, can be used in comparatively high concentrations. It has been found that the compounds are suitable in a very advantageous manner for TFT applications.

In the above definition of the compounds of formula I the terms "1E-alkenyl", "3E-alkenyl" and "4-alkenyl" for $R^3$ embrace exclusively alkenyl groups in which in each case a single double bond is present and is situated in the 1,2-, 3,4- or 4,5-position. Moreover, the part of the 1E-, 3E- or 4-alkenyl group or alkoxyalkyl group $R^{3'}$ which is situated between ring C and the double bond or the oxygen atom, is always straight-chain; the remaining (terminal) part of this alkenyl or alkoxyalkyl group can be straight-chain or branched. The term "halogen" means fluorine, chlorine, bromine or iodine.

Not only the position of the nitrogen atom or the nitrogen atoms in the pyridine-2,5-diyl ring or pyrimidine-2,5-diyl ring (ring A or B), but also the position of the oxygen atoms of the trans-1,3-dioxane-2,5-diyl ring (ring C) are directed only in the direction of the halogenated phenyl group

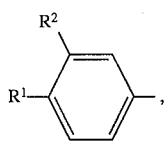

i.e., such a ring which may be present in the above formula I is arranged from left to right as follows:

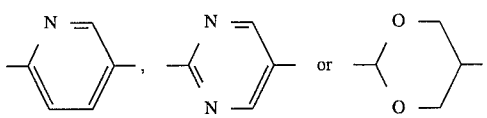

Under the term "saturated ring" which appears in the definition of $Z^1$ and $Z^2$ there is to be understood trans-1,4-cyclohexylene ring (ring A and/or ring B). The term "(hetero)aromatic" which appears in proviso (a) relates to ring B when this signifies 1,4-phenylene, which is unsubstituted or mono- or disubstituted with halogen and/or cyano and/or methyl; pyridine-2,5-diyl; or pyrimidine-2,5-diyl, i.e., when ring B is different from trans-1,4-cyclohexylene.

Ring A is preferably trans-1,4-cyclohexylene or optionally substituted 1,4-phenylene (as is described above in more detail) and ring B is preferably trans-1,4-cyclohexylene, followed by optionally substituted 1,4-phenylene. Preferably, $Z^1$ signifies a single bond, $Z^2$ and $Z^3$ do not both signify ethylene and $R^3$ signifies vinyl, 1E-propenyl, 1E- or 3-butenyl, 1E-, 3E- or 4-pentenyl, 1E- or 3E hexenyl or 1E- or 3E heptenyl. Where ring A or B signifies optionally substituted 1,4-phenylene, this is in each case preferably unsubstituted 1,4-phenylene.

Formula I preferably embraces the compounds of the following general formulae:

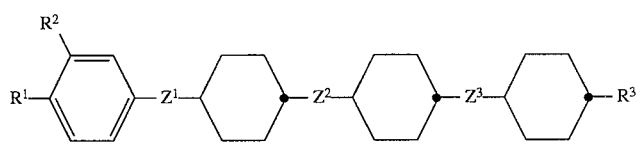

Ia

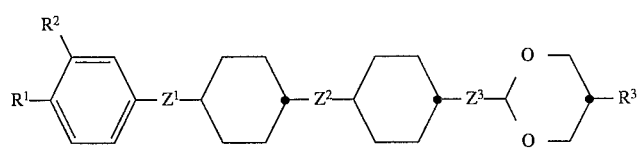

Ib

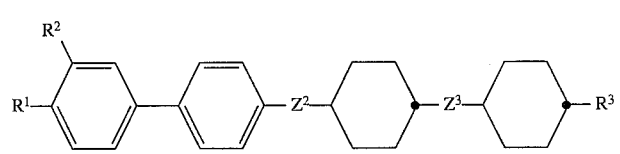

Ic

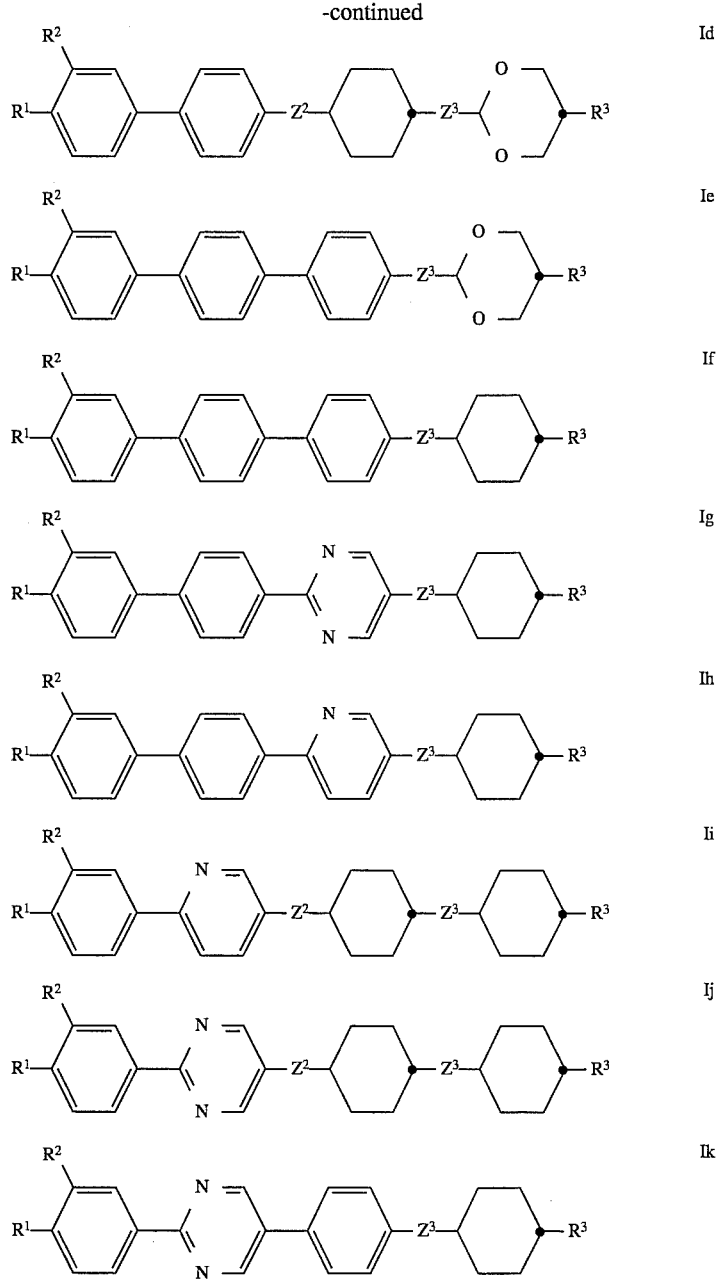

Individual representatives of the compounds of formula I are:

trans-5-(1E-Butenyl)-2-{trans-4'-(4-chlorophenyl)-[1,1'-bicyclohexyl]-trans-4-yl}-1,3-dioxane,
trans-5-(1E-pentenyl)-2-{trans-4'-(4-chlorophenyl)-[1,1'-bicyclohexyl]-trans-4-yl}-1,3-dioxane,
trans-5-(4-pentenyl)-2-{trans-4'-(4-chlorophenyl)-[1,1'-bicyclohexyl]-trans-4-yl}-1,3-dioxane,
trans-5-(3-methoxypropyl)-2-{trans-4'-(4-chlorophenyl)-[1,1'-bicyclohexyl] -trans-4-yl}-1,3-dioxane,
trans-5-(1E-propenyl)-2-{trans-4'-(4-chloro-3-fluorophenyl)-[1,1'-bicyclohexyl] -trans-4-yl}-1,3-dioxane,
trans-5-(3-butenyl)-2-{trans-4'-(4-chloro-3-fluorophenyl)-[1,1'-bicyclohexyl] -trans-4-yl}-1,3-dioxane,
trans-5-(3-methoxypropyl)-2-{trans-4'-(4-chloro-3-fluorophenyl)-[1,1'-bicyclohexyl] -trans-4-yl}-1,3-dioxane,
trans-5-(1E-propenyl)-2-{trans-4'-(3,4-difluorophenyl)-[1,1'-bicyclohexyl] -trans-4-yl}-1,3-dioxane,
trans-5-(1E-butenyl)-2-{trans-4'-(3,4-difluorophenyl)-[1,1'-bicyclohexyl]-trans-4-yl }-1,3-dioxane,
trans-5-(1E-pentenyl)-2-{trans-4'-(3,4-difluorophenyl)-[1,1'-bicyclohexyl] -trans-4-yl}-1,3-dioxane,
trans-5-(3-butenyl)-2-{trans-4'-(3,4-difluorophenyl)-[1,1'-bicyclohexyl]-trans-4-yl}-1,3-dioxane,
trans-5-(3-methoxypropyl)-2-{trans-4'-(3,4-difluorophenyl)-[1,1'-bicyclohexyl] -trans-4-yl}-1,3-dioxane,
trans-5-(1E-propenyl)-2-{trans-4'-(4-fluorophenyl)-[1,1'-bicyclohexyl]-trans-4-yl}-1,3-dioxane,
trans-5-(3-methoxypropyl)-2-{trans-4'-(4-fluorophenyl)-[1,1'-bicyclohexyl] -trans-4-yl}-1,3-dioxane,
trans-5-(1E-pentenyl)-2-{trans-4'-(4-chlorophenethyl)-[1,1'-bicyclohexyl] -trans-4-yl}-1,3-dioxane, trans-5-(4-pentenyl)-2-{trans-4'-(4-chlorophenethyl)-[1,1'-bicyclohexyl]-trans-4-yl}-1,3-dioxane,
trans-5-(3-methoxypropyl)-2-{trans-4'-(4-chlorophenethyl)-[1,1'-bicyclohexyl] -trans-4-yl}-1,3-dioxane,
trans-5-(1E-propenyl)-2-{trans-4'-(4-chloro-3-fluorophenethyl)-[1,1' -bicyclohexyl]-trans-4-yl}-1,3-dioxane,
trans-5-(3-butenyl)-2-[trans-4'-(4-chloro-3-fluorophenethyl)-[1,1'-bicyclohexyl] -trans-4-yl]-1,3-dioxane,
trans-5-(1E-propenyl)-2-{trans-4'-(3,4-difluorophenethyl)-[1,1'-bicyclohexyl] -trans-4-yl}-1,3-dioxane,
trans-5-(1E-butenyl)-2-{trans-4'-(3,4-difluorophenethyl)-[1,1'-bicyclohexyl] -trans-4-yl}-1,3-dioxane,
trans-5-(1E-pentenyl)-2-{trans-4'-(3,4-difluorophenethyl)-[1,1'-bicyclohexyl] -trans-4-yl}-1,3-dioxane,
trans-5-(3-butenyl)-2-{trans-4'-(3,4-difluorophenethyl)-[1,1'-bicyclohexyl] -trans-4-yl}-1,3-dioxane,
trans-5-(3-methoxypropyl)-2-{trans-4'-(3,4-difluorophenethyl)-[1,1'-bicyclohexyl] -trans-4-yl}-1,3-dioxane,
trans-5-(3-methoxypropyl)-2-{trans-4'-(4-fluorophenethyl)-[1,1'-bicyclohexyl] -trans-4-yl}-1,3-dioxane,
trans-5-(1E-propenyl)-2-[2-{trans-4'-(4-chlorophenyl)-[1,1'-bicyclohexyl] -trans-4-yl}-1,3-dioxane,
trans-5-(3-butenyl)-2-[2-{trans-4'-(4-chlorophenyl)-[1,1'-bicyclohexyl]-trans-4-yl}-1,3-dioxane,
trans-5-(3-butenyl)-2-[2-trans-4'-(3,4-difluorophenyl)-[1,1'-bicyclohexyl] -trans-4-yl}-1,3-dioxane,
trans-5-(3-methoxypropyl)-2-[2-trans-4'-(4-fluorophenyl)-[1,1'-bicyclohexyl] -trans-4-yl}-1,3-dioxane,
trans-5-(1E-propenyl)-2-[2-trans-4'-(4-chloropenethyl)-[1,1'-bicyclohexyl] -trans-4-yl]-1,3-dioxane,
trans-5-(1E-propenyl)-2-[trans-4-(4'-chloro-4-biphenylyl)-cyclohexyl]-1,3-dioxane,
trans-5-(1E-pentenyl)-2-[trans-4-(4'-chloro-4-biphenylyl)-cyclohexyl]-1,3-dioxane,
trans-5-(3-butenyl)-2-[trans-4-(4'-chloro-4-biphenylyl)-cyclohexyl]-1,3-dioxane,
trans-5-(4-pentenyl)-2-[trans-4-(4'-chloro-4-biphenylyl)-cyclohexyl]-1,3-dioxane,
trans-5-(3-methoxypropyl)-2-[trans-4-(4'-chloro-4-biphenylyl)-cyclohexyl]-1,3-dioxane,
trans-5-(1E-propenyl)-2-[trans-4-(4'-chloro-3'-fluoro-4-biphenylyl)-cyclohexyl] -1,3-dioxane,
trans-5-(3-butenyl)-2-[trans-4-(4'-chloro-3'-fluoro-4-biphenylyl)-cyclohexyl] -1,3-dioxane,
trans-5-(1E-propenyl)-2-[trans-4-(3',4'-difluoro-4-biphenylyl)-cyclohexyl] -1,3-dioxane,
trans-5-(3-butenyl)-2-[trans-4-(3',4'-difluoro-4-biphenylyl)-cyclohexyl] -1,3-dioxane,
trans-5-(3-methoxypropyl)-2-[trans-4-(3',4'-difluoro-4-biphenylyl)-cyclohexyl] -1,3-dioxane,
trans-5-(4-pentenyl)-2-[trans-4-(4'-fluoro-4-biphenylyl)-cyclohexyl]-1,3-dioxane,
trans-5-(3-methoxypropyl)-2-[trans-4-(4'-fluoro-4-biphenylyl)-cyclohexyl] -1,3-dioxane,
trans-5-(1E-propenyl)-2-{trans-4-[2-(4'-chloro-4-biphenylyl)-ethyl-cyclohexyl} -1,3-dioxane,
trans-5-(3-butenyl)-2-{trans-4-[2-(4'-chloro-4-biphenylyl)-ethyl]-cyclohexyl}-1,3-dioxane,
trans-5-(1E-propenyl)-2-{trans-4-[2-(3',4'-difluoro-4-biphenylyl)-ethyl] -cyclohexyl}-1,3-dioxane,
trans-5-(3-butenyl)-2-{trans-4-[2-(3',4'-difluoro-4-biphenylyl)-ethyl] -cyclohexyl}-1,3-dioxane,
trans-5-(3-methoxypropyl)-2-{trans-4-[2-(4'-fluoro-4-biphenylyl)-ethyl] -cyclohexyl}-1,3-dioxane,
trans-5-(3-butenyl)-2-(4''-chloro-p-terphenyl-4-yl)-1,3-dioxane,
trans-5-(3-methoxypropyl)-2-(4''-fluoro-p-terphenyl-4-yl)-1,3-dioxane,
trans-5-(3-butenyl)-2-[2-(4''-fluoro-p-terphenyl-4-yl)-ethyl] -1,3-dioxane,
trans-5-(trans-4-vinylcyclohexyl)-2-[trans-4-(4-chlorophenyl)-cyclohexyl]-1,3-dioxane,
trans-5-[trans-4-(3-butenyl)-cyclohexyl]-2-[trans-4-(4-chlorophenyl)-cyclohexyl] -1,3-dioxane,
trans-5-[trans-4-(3-methoxypropyl)-cyclohexyl]-2-[trans-4-(4-chlorophenyl)-cyclohexyl] -1,3-dioxane,
trans-5-(trans-4-vinylcyclohexyl)-2-[trans-4-(3,4-difluorophenyl)-cyclohexyl]-1,3-dioxane,
trans-5-[trans-4-(3-butenyl)-cyclohexyl]-2-[trans-4-(3,4-difluorophenyl)-cyclohexyl] -1,3-dioxane,
trans-5-[trans-4-(3-methoxypropyl)-cyclohexyl]-2-[trans-4-(4-fluorophenyl)-cyclohexyl] -1,3-dioxane,
trans-5-(trans-4-vinylcyclohexyl)-2-{2-[trans-4-(4-chlorophenyl)-cyclohexyl]-ethyl} -1,3-dioxane,
trans-5-[trans-4-(3-butenyl)-cyclohexyl]-2-{2-[trans-4-(4-chlorophenyl)-cyclohexyl] -ethyl}-1,3-dioxane,
trans-5-[trans-4-(3-butenyl)-cyclohexyl]-2-{2-[trans-4(3,4-difluorophenyl)-cyclohexyl] -ethyl}-1,3-dioxane,
trans-5-(trans-4-vinylcyclohexyl)-2-(4'-chloro-4-biphenylyl)-1,3-dioxane,
trans-5-[trans-4-(3-butenyl)-cyclohexyl-]2-(4'-chloro-4-biphenylyl)-1,3-dioxane,
trans-5-[trans-4-(3-butenyl)-cyclohexyl]-2-(3',4'-difluoro-4-biphenylyl)-1,3-dioxane,
trans-5-[trans-4-(3-methoxypropyl)-cyclohexyl]-2-(4'-fluoro-4-biphenylyl)-1,3-dioxane,
trans-5-[trans-4-(3-butenyl)-cyclohexyl]-2-[2-(4'-chloro-4-biphenylyl)-ethyl] -1,3-dioxane,
4-[trans-4'-vinyl-(1,1'-bicyclohexyl)-trans-4-yl]-3',4'-difluorobiphenyl,
4-[trans-4'-(1E-pentenyl)-[1,1'-bicyclohexyl]-trans-4-yl}-3',4'-difluorobiphenyl,
4-[trans-4'-(3-butenyl)-[1,1'-bicyclohexyl]-trans-4-yl}-3',4' -difluorobiphenyl,
4-[trans-4'-(3E-pentenyl)-[1,1'-bicyclohexyl]-trans-4-yl}-3',4'-difluorobiphenyl,
4-[trans-4'-(4-pentenyl)-[1,1'-bicyclohexyl]-trans-4-yl}-4'-fluorobiphenyl,
4-{trans-4'-vinyl-(1,1'-bicyclohexyl)-trans-4-yl}-4'-chlorobiphenyl,
4-{trans-4'-IE-propenyl)-[1,1'-bicyclohexyl]-trans-4-yl}-4'-chlorobiphenyl,
4-{trans-4'-(3-butenyl)-[1,1'-bicyclohexyl]-trans-4-yl}-4'-chlorobiphenyl,
4-{trans-4'-(3E-pentenyl)-[1,1'-bicyclohexyl]-trans-4-yl}-4'-chlorobiphenyl,
4-[trans-4'-vinyl-(1',1'-bicyclohexyl)-trans-4'-chloro-3'-fluorobiphenyl,
4-{trans-4'-(3-butenyl)-[1,1'-bicyclohexyl]-trans-4-yl}-4'-chloro-3' -fluorobiphenyl,
4-{2-[trans-4'-vinyl-(1,1'-bicyclohexyl)-trans-4-yl]-ethyl}-3',4' -difluorobiphenyl,
4-[2-{trans-4'-(1E-propenyl)-[1,1'-bicyclohexyl]-trans-4 -yl]-ethyl}-3',4'-difluorobiphenyl,
4-[2-{trans-4'-(3-butenyl)-[1,1'-bicyclohexyl]-trans-4-yl}-ethyl] -3',4'-difluorobiphenyl,
4-{2-[trans-4'-vinyl-(1,1'-bicyclohexyl)-trans-4-yl]-ethyl}-4'-chlorobiphenyl,
4-[2-{trans-4'-(3-butenyl)-[1,1'-bicyclohexyl]-trans-4-yl}ethyl]-4'-chlorobiphenyl,
4-{trans-4-[2-(trans-4-vinylcyclohexyl)-ethyl]-cyclohexyl}-3',4'-difluorobiphenyl,
4-[trans-4-{2-[trans-4(3-butenyl)-cyclohexyl]-ethyl}-cyclohexyl]-4'-chlorobiphenyl, trans-4-[2-(trans-4-vinylcyclohexyl)-ethyl]-trans-4'-(3,4-difluorophenyl)-1,1'-bicyclohexyl,
trans-4-{2-[trans-4-(1E-propenyl)-cyclohexyl]-ethyl}-trans-4'-(3,4-difluorophenyl)-1,1'-bicyclohexyl,
trans-4-{2-[trans-4-(3-butenyl)-cyclohexyl]-ethyl}-trans-4'-(3,4-difluorophenyl)-1,1'-bicyclohexyl,
trans-4-{2-[trans-4-(4-pentenyl)-cyclohexyl]-ethyl}-trans-4'-(4-fluorophenyl)-1,1'-bicyclohexyl,
trans-4-[2-(trans-4-vinylcyclohexyl)-ethyl]-trans-4'-(4-chloro-3-fluorophenyl)-1,1'-bicyclohexyl,
trans-4-[2-(trans-4-vinylcyclohexyl)-ethyl]-trans-4'-(4-chlorophenyl)-1,1'-bicyclohexyl,
trans-4-{2-[trans-4-(1E-propenyl)-cyclohexyl]-ethyl}-trans-4'-(4-chloro-3-fluorophenyl)-1,1'-bicyclohexyl,
trans-4-{2-[trans-4-(3-butenyl)-cyclohexyl]-ethyl}-trans-4'-(4-chloro-3-fluorophenyl)-1,1'-bicyclohexyl,
trans-4-vinyl-trans-4'-{2-[trans-4-(3,4-difluorophenyl)-cyclohexyl]-ethyl}-1,1'-bicyclohexyl,
trans-4-(1E-propenyl)-trans-4'-{2-[trans-4-(3,4-difluorophenyl)-cyclohexyl]-ethyl}-1,1'-bicyclohexyl,
trans-4-vinyl-trans-4'-{2-[trans-4(4-chlorophenyl)-cyclohexyl]-ethyl}-1,1'-bicyclohexyl,
trans-4-(1E-propenyl)-trans-4'-{2-[trans-4-(4-chlorophenyl)-cyclohexyl]-ethyl}-1,1'-bicyclohexyl,
trans-4-(3-butenyl)-trans-4'-{2-[trans-4-(4-chlorophenyl)-cyclohexyl]-ethyl}-1,1'-bicyclohexyl,
4-(trans-4-vinylcyclohexyl)-3",4"-difluoro-p-terphenyl,
4-[trans-4-(3-butenyl)-cyclohexyl]-4"-chloro-p-terphenyl,
4-[2-(trans-4-vinylcyclohexyl)-ethyl]-3",4"-difluoro-p-terphenyl,
4-{2-[trans-4-(3-butenyl)-cyclohexyl]-ethyl}-4"-chloro-p-terphenyl,
5-[trans-4'-vinyl-(1,1'-bicyclohexyl)-trans-4-yl]-2-(3,4-difluorophenyl)-pyridine,
5-[trans-4'-vinyl-(1,1'-bicyclohexyl)-trans-4-yl]-2-(4-chlorophenyl)-pyridine,
5-{2-[trans-4'-vinyl-(1,1'-bicyclohexyl)-trans-4-yl]-ethyl}-2-(3,4-difluorophenyl)-pyridine,
5-[2-{trans-4'-(1E-propenyl)-[1,1'-bicyclohexyl]-trans-4-yl}-ethyl] -2-(3,4-difluorophenyl)-pyridine,
5-[2-{trans-4'-(3-butenyl)-[1,1'-bicyclohexyl]-trans-4-yl}ethyl]-2-(3,4-difluorophenyl)-pyridine,
5-[2-{trans-4'-(4-pentenyl)-[1,1'-bicyclohexyl]-trans-4-yl}-ethyl] -2-(4-fluorophenyl)-pyridine,
5-{2-[trans-4'-vinyl-(1,1'-bicyclohexyl)-trans-4-yl]-ethyl} -2-(4-chloro-3-fluorophenyl)-pyridine,
5-{2-[trans-4'-vinyl-(1,1'-bicyclohexyl)-trans-4-yl]-ethyl} -2-(4-chlorophenyl)-pyridine,
5-[2-{trans-4'-(1E-propenyl)-[1,1'-bicyclohexyl]-trans-4-yl}-ethyl] -2-(4-chlorophenyl)-pyridine,
5-[2-{trans-4'-(3-butenyl)-[1,1'-bicyclohexyl]-trans-4-yl}ethyl]-2-(4-chlorophenyl)-pyridine, 4-{trans-4'-(3-methoxypropyl)-[1,1'-bicyclohexyl]-trans-4-yl}-4'-fluorobiphenyl,
4-{trans-4'-(3-methoxypropyl)-[1,1'-bicyclohexyl]-trans-4-yl} -4'-chloro-3'-fluorobiphenyl,
4-{trans-4'-(3-methoxypropyl)-[1,1'-bicyclohexyl]-trans-4-yl}-4'-chlorobiphenyl, 4-[2-{trans-4'-(3-methoxypropyl)-[1,1'-bicyclohexyl]-trans-4-yl}-ethyl] -3',4'-difluorobiphenyl,
4-[2-{trans-4'-(3-methoxypropyl)-[1,1'-bicyclohexyl]-trans-4-yl}-ethyl] -3',4'-fluorobiphenyl,
4-[2-{trans-4'-(3-methoxypropyl)-[1,1'-bicyclohexyl]-trans-4-yl}-ethyl] -4'-chloro-3'-fluorobiphenyl,
trans-4-{2-[trans-4-(3-methoxypropyl)-cyclohexyl]-ethyl}-trans-4' -(4-fluorophenyl)-1,1'-bicyclohexyl,
trans-4-{2-[trans-4-(3-methoxypropyl)-cyclohexyl]-ethyl}-trans-4' -(4-chlorophenyl)-1,1'-bicyclohexyl,
5-[2-{trans-4'-(3-methoxypropyl)-[1,1'-bicyclohexyl]-trans-4-yl}-ethyl] -2-(3,4-difluorophenyl)-pyridine,
5-[2-{trans-4'-(3-methoxypropyl)-[1,1'-bicyclohexyl]-trans-4-yl}-ethyl] -2-(4-fluorophenyl)-pyridine,
5-[2-{trans-4'-(3-methoxypropyl)-[1,1'-bicyclohexyl]-trans-4-yl}-ethyl] -2-(4-chlorophenyl)-pyridine,
5-{trans-4'-vinyl-[1,1'-bicyclohexyl]-trans-4-yl}-2-(4-chlorophenyl)-pyrimidine,
5-{trans-4'-(3-butenyl)-[1,1'-bicyclohexyl]-trans-4-yl}-2 -(4-chlorophenyl)-pyrimidine,
5-{trans-4'-(3-methoxypropyl)-[1,1'-bicyclohexyl]-trans-4-yl}-2 -(4-chlorophenyl)-pyrimidine,
5-{trans-4'-(4-pentenyl)-1,1'-bicyclohexyl-trans-4-yl}-2 -(4-fluorophenyl)-pyrimidine,
5-{trans-4'-(3-methoxypropyl)-[1,1'-bicyclohexyl]-trans-4-yl} -2-(4-fluorophenyl)-pyrimidine,
5-{trans-4'-(1E-[propenyl)-[1,1'-bicyclohexyl]-trans-4-yl} -2-(3,4-difluorophenyl)-pyrimidine,
5-[2-{trans-4'-vinyl-[1,1'-bicyclohexyl]-trans-4-yl}-ethyl] -2-(4-chlorophenyl)-pyrimidine,
5-[2-{trans-4'-(3-butenyl)-[1,1'-bicyclohexyl]-trans-4-yl}-ethyl]-2-(4-chlorophenyl)-pyrimidine,
5-[2-{trans-4'-(3-methoxypropyl)-[1,1'-bicyclohexyl]-trans-4-yl}-ethyl] -2-(4-fluorophenyl)-pyrimidine and
5-[2-{trans-4'-(1E-propenyl)-[1,1'-bicyclohexyl]-trans-4-yl}-ethyl] -2-(3,4-difluorophenyl)-pyrimidine.

The compounds of formula I can be manufactured according to known synthetic methods in accordance with the following Reaction Schemes 1–7, of which Schemes 1a, 1b and 2 represent the manufacture of the end products I and Schemes 3a, 3b and 4–7 represent the production of the important intermediates or starting materials from known compounds or compounds obtainable in a known manner. The methods used, e.g. the Wittig reaction, the Grignard reaction, hydrolyses, reductions, halogenations and other known synthetic steps are amply described in the technical literature and will be familiar to any person skilled in the art.

Reaction Scheme 1a (synthesis of the alkenyl group R³)
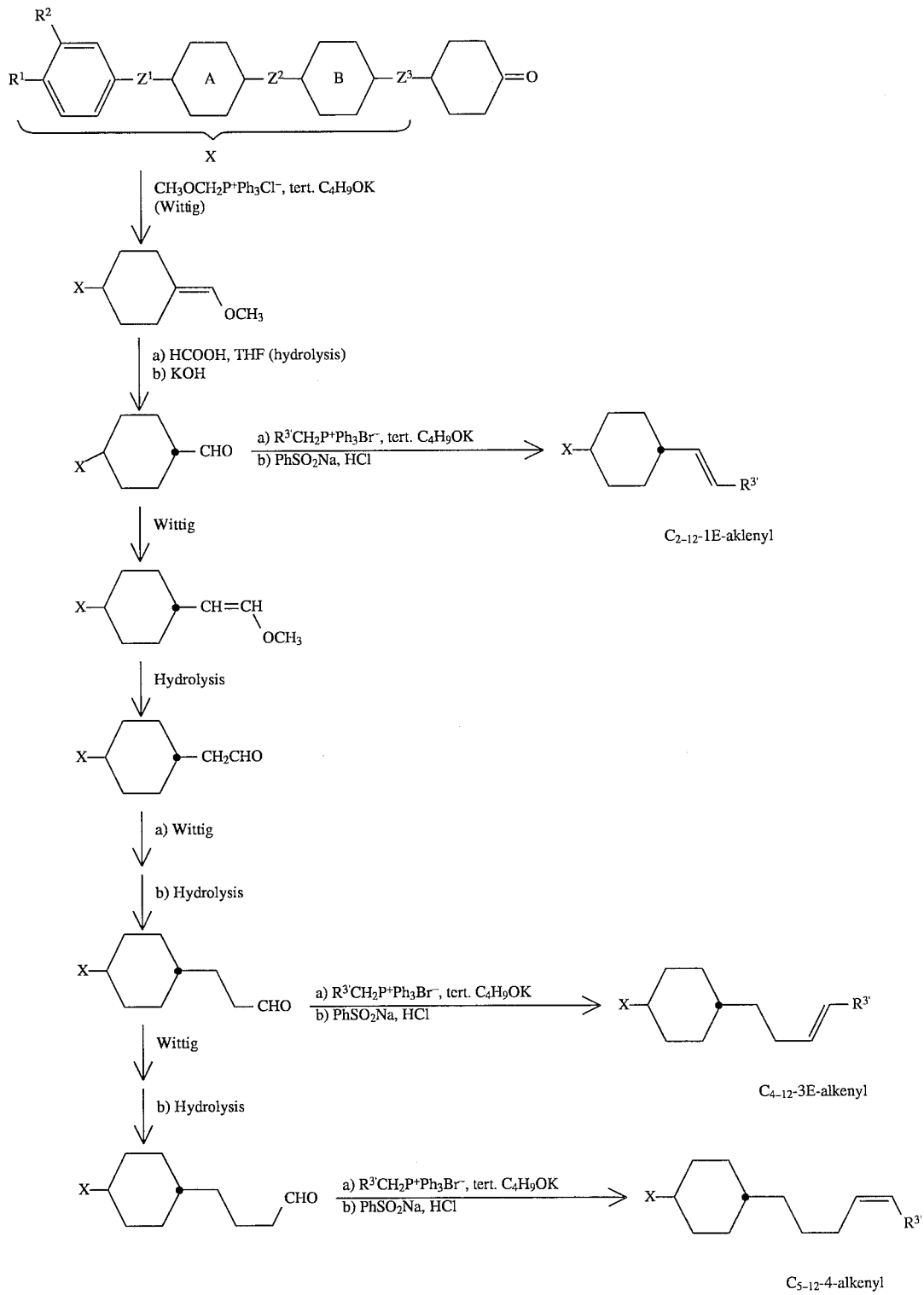

-continued
Reaction Scheme 1a (synthesis of the alkenyl group $R^3$)

Legends:

X = (see above)
Ph = phenyl
THF = tetrahydrofuran
$R^{3'}$ = terminal part of the $C_{2-12}$-1E-alkenyl, $C_{4-12}$-3E-alkenyl- or $C_{5-12}$-4-alkenyl group $R^3$

10

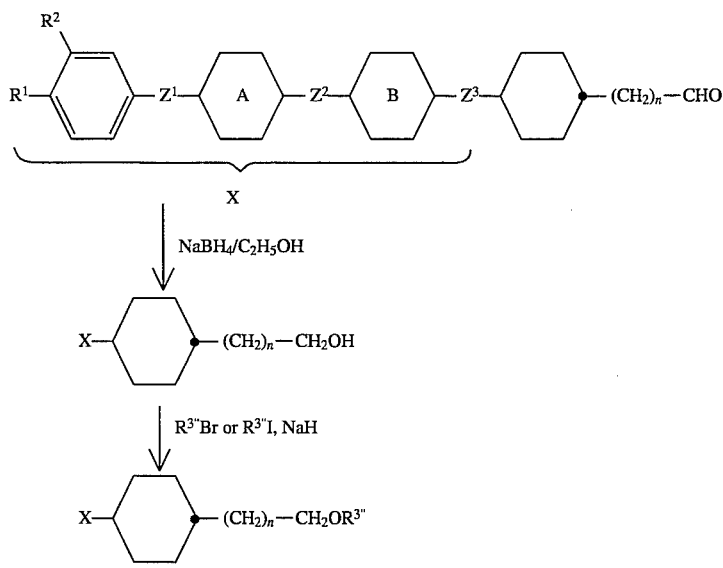

Reaction Scheme 1b (synthesis of the alkoxyalkyl group $R^3$)

Legends:

X = (see above)
n = 0–4
$R^{3''}$ = terminal part of the $C_{2-12}$-alkoxyalkyl group $R^3$, i.e. $C_{1-11}$-alkyl depending on the value of n (total number of carbon atoms in $-(CH_2)_n-CH_2OR^{3''}$ = 2–12)

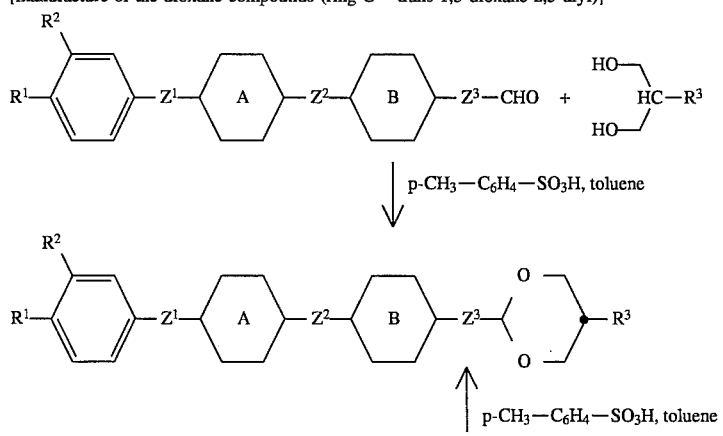

Reaction Scheme 2
[manufacture of the dioxane compounds (ring C = trans-1,3-dioxane-2,5-diyl)]

-continued
Reaction Scheme 2
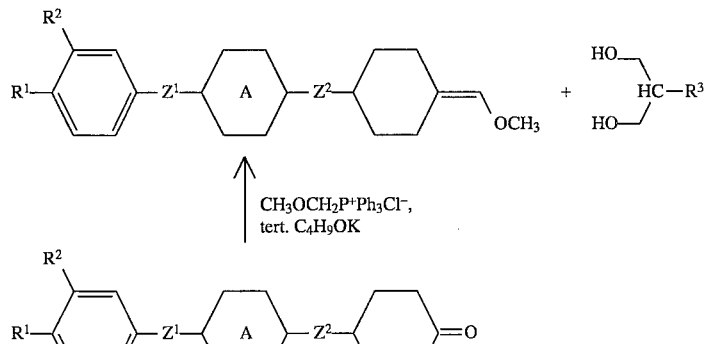
Reaction Scheme 3a
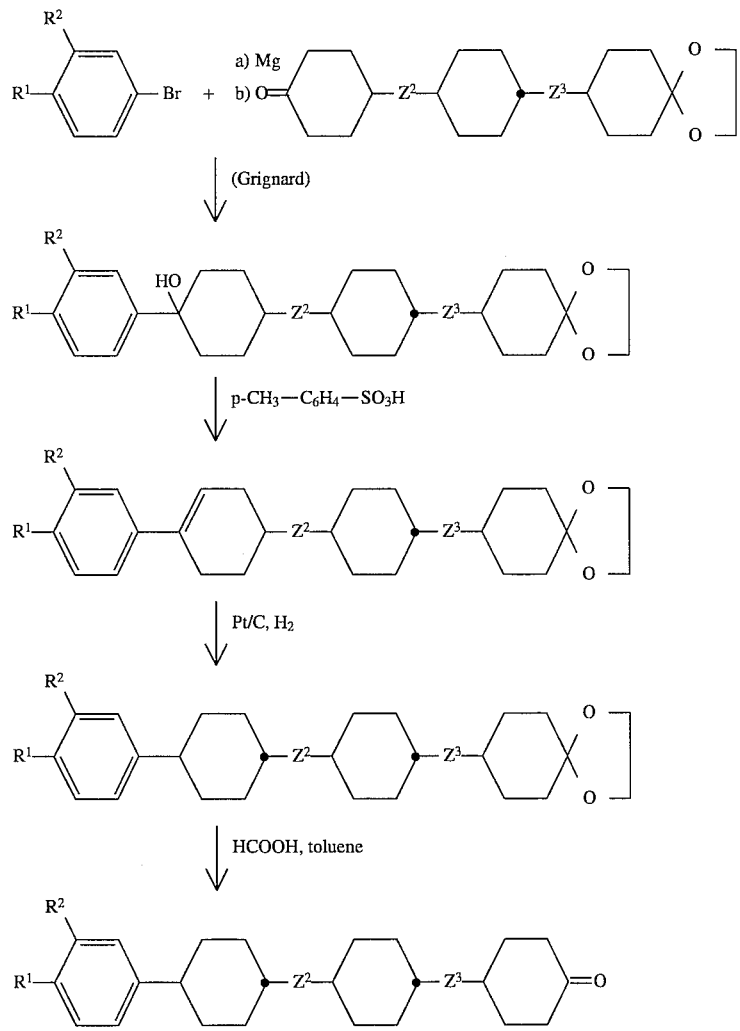

Reaction Scheme 3b
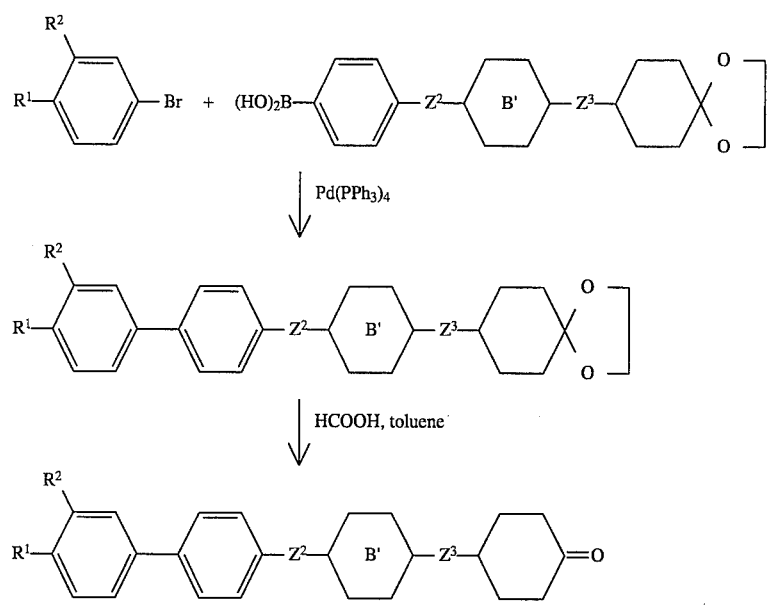
Legends:
 B' = trans-1,4-cyclohexylene or 1,4-phenylene, which is unsubstituted or mono- or disubstituted with halogen and/or cyano and/or methyl
Ph = phenyl
Reaction Scheme 4
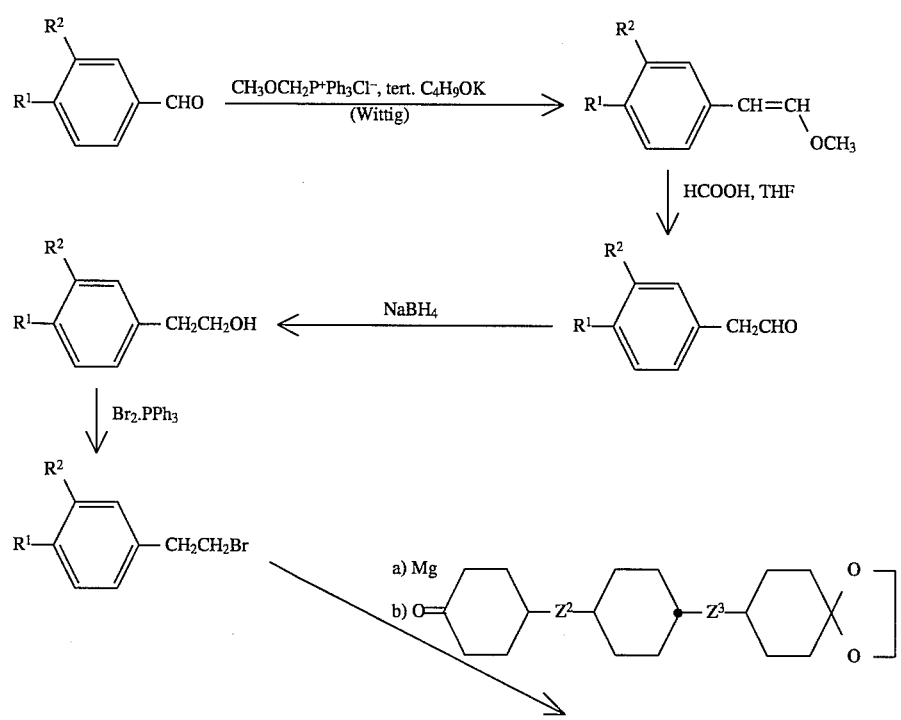

-continued
Reaction Scheme 4
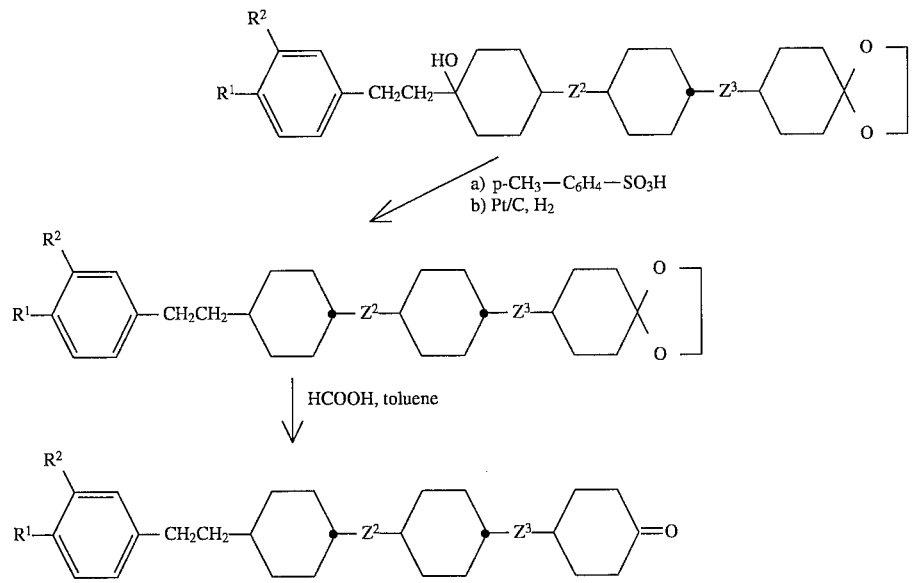
Legends:
Ph = phenyl
THF = tetrahydrofuran
Reaction Scheme 5
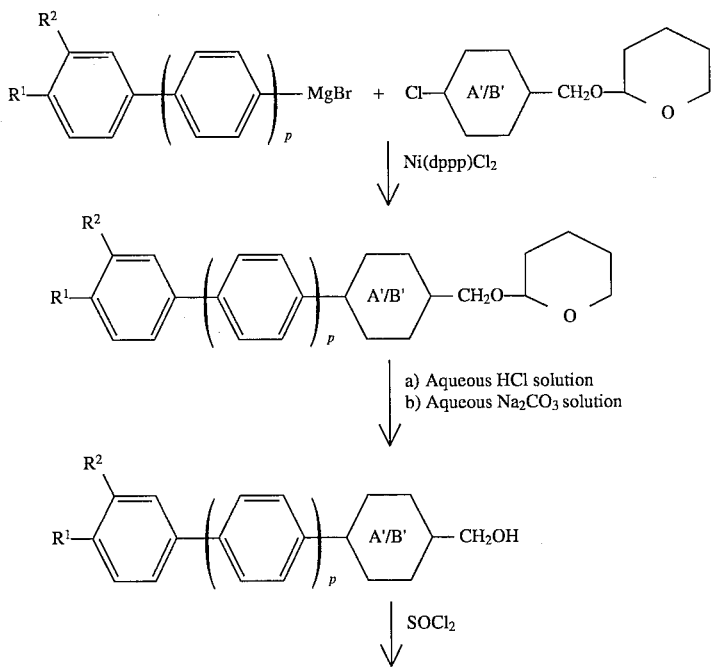

-continued
Reaction Scheme 5
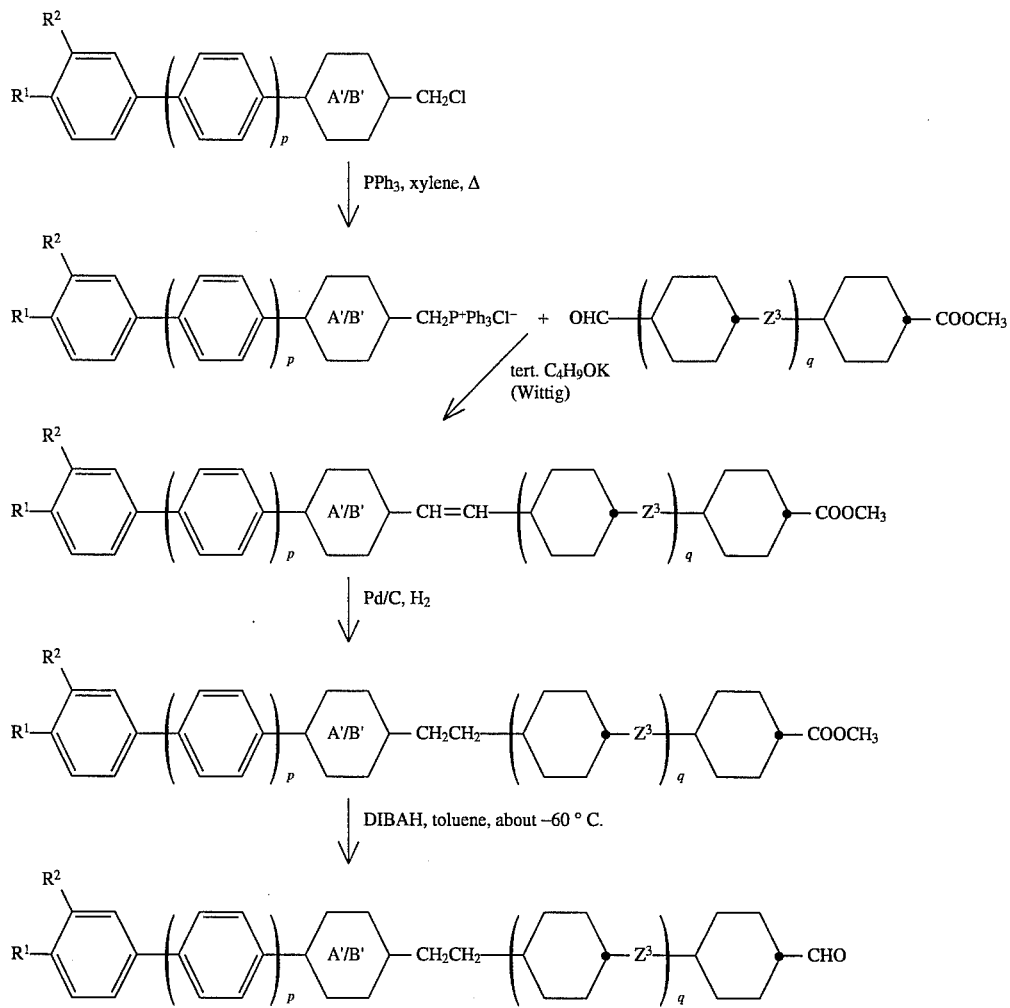
Legends:
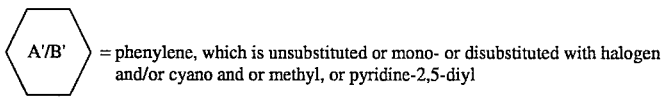 = phenylene, which is unsubstituted or mono- or disubstituted with halogen and/or cyano and or methyl, or pyridine-2,5-diyl
p = 0 and q = 1 or p = 1 and q = 0
Ni(dppp)Cl$_2$ = 1,3-bis(diphenylphosphino)-propane-nickel(II)chloride
Ph = phenyl
DIBAH = diisobutylaluminium hydride
Reaction Scheme 6
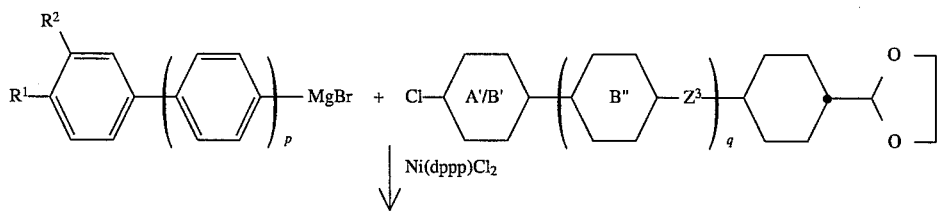

-continued
Reaction Scheme 6

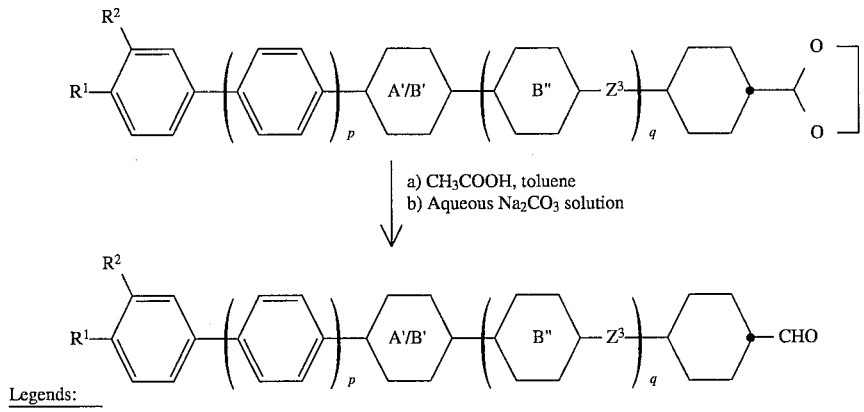

a) CH₃COOH, toluene
b) Aqueous Na₂CO₃ solution

Legends:

 = 1,4-phenylene, which is unsubstituted or mono- or disubstituted with halogen and/or cyano and/or methyl, or pyridine-2,5-diyl

 = trans-1,4-cyclohexylene or 1,4-phenylene, which is unsubstituted or mono- or disubstituted with halogen and/or cyano and/or methyl p = 0 and q = 1 or p = 1 and q = 0
Ni(dppp)Cl₂ = 1,3-bis(diphenylphosphino)-propane-nickel(II)chloride Reaction Scheme 7

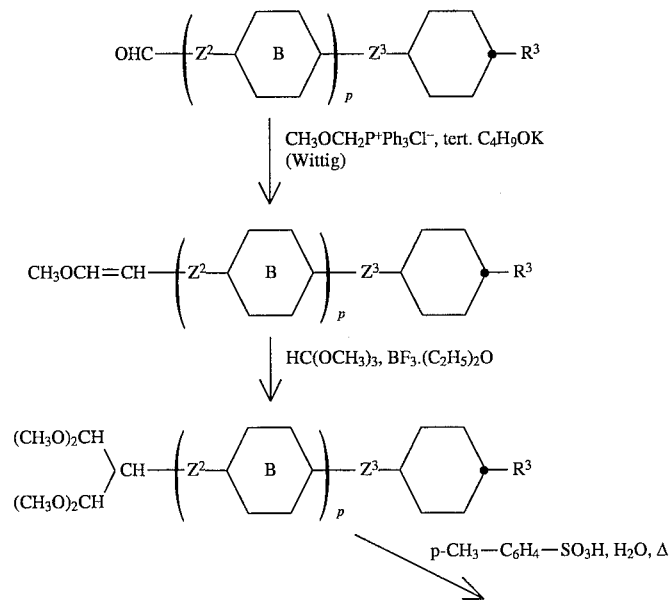

-continued
Reaction Scheme 7

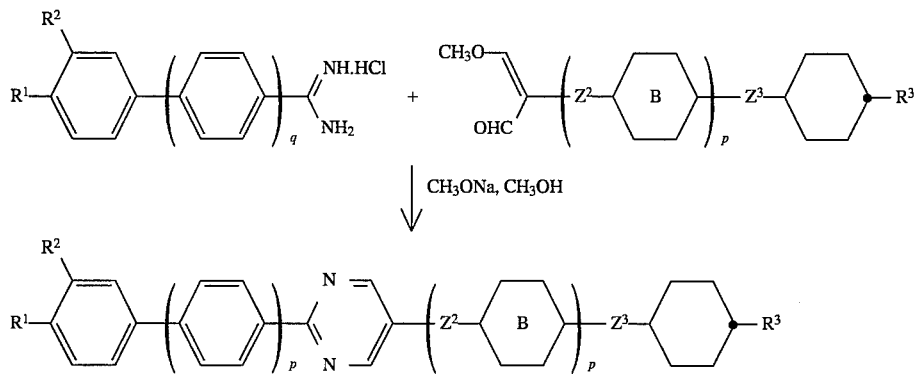

Legends:

Ph = phenyl
p = 0 and q = 1 or p = 1 and q = 0

When $R^3$ is different from vinyl or $C_{2-12}$-alkoxyalkyl, E/Z mixtures are generally obtained which can be separated according to known methods, e.g., by chromatography on silica gel impregnated with silver nitrate. Further, if desired, the E/Z mixtures or the Z-isomers can be converted predominantly into the E-form by equilibration with sulphinic acids, e.g. benzenesulphinic acid or p-toluenesulphinic acid.

The compounds of formula I can be used in the form of mixtures with one another and/or with other liquid crystal components, for example, with substances from the classes of azoxybenzenes, phenylbenzoates, cyclohexanecarboxylic acid phenyl esters, cyclohexanecarboxylic acid cyclohexyl esters, biphenyls, tolanes, phenylcyclohexanes, cyclohexylcyclohexanes, phenylpyrimidines, phenylpyridines, cyclohexylpyrimidines, cyclohexylpyridines, phenyldioxanes, 2-cyclohexyl-1-phenylethanes, terphenyls, cyclohexylbiphenyls, bicyclohexylphenyls, cyclohexylphenylpyrimidines, phenylcyclohexyldioxanes and dicyclohexylbiphenyls. Such substances will be known to a person skilled in the art and many of them are commercially available.

The liquid crystalline mixtures, in accordance with the invention, contain at least two components, of which at least one component is a compound of formula I. A second component and optionally further components can be additional compounds of formula I or other liquid crystal components. The compounds of formula I are especially suitable for nematic mixtures or, insofar as at least one component of the mixture is optically active, also for cholesteric mixtures.

Given the good solubility of the compounds of formula I and given their good miscibility with one another, their content in the mixtures in accordance with the invention can be relatively high. In general, however, a content of about 1–50 wt. %, especially about 2–30 wt. %, of compounds of formula I is preferred.

Preferably, the mixtures in accordance with the invention contain, in addition to one or more compounds of formula I, one or more compounds from the group of compounds of the general formulae:

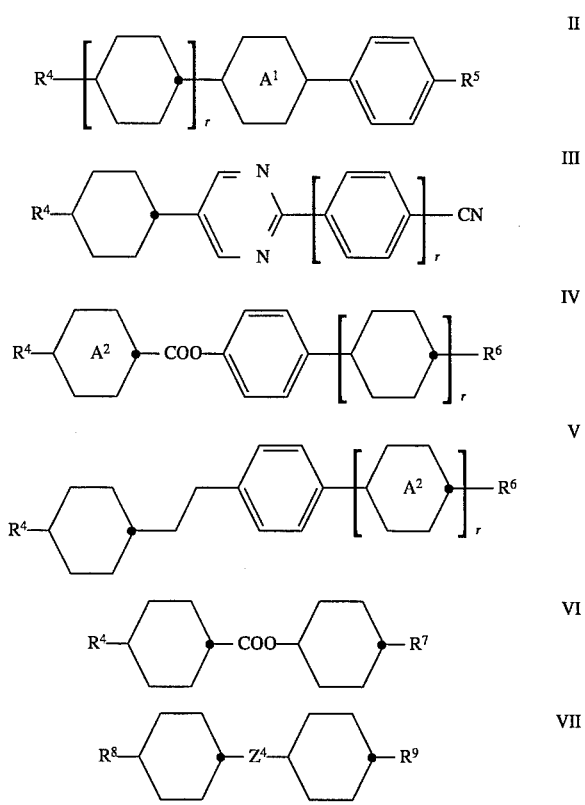

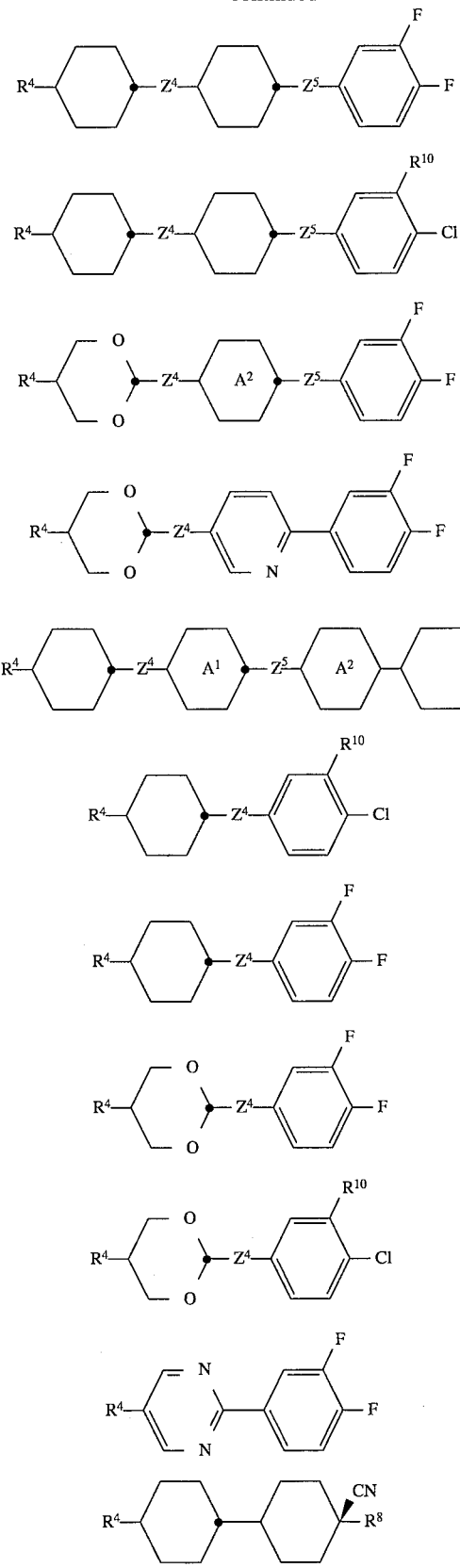

wherein r stands for the number 0 or 1; $R^4$ and $R^7$ each independently signify alkyl, alkoxyalkyl, 3E-alkenyl, 4-alkenyl or on a saturated ring also 1E-alkenyl; ring $A^1$ represents 1,4-phenylene, trans-1,4-cyclohexylene, pyridine-2,5-diyl, pyrimidine-2,5-diyl or trans-1,3-dioxane-2,5-diyl; $R^5$ denotes cyano, isothiocyanato, fluorine, alkyl, 3E-alkenyl, 4-alkenyl, alkoxy, 2E-alkenyl-oxy, 3-alkenyloxy or 1-alkynyl; ring $A^2$ represents,4-phenylene or trans-1,4-cyclohexylene; $R^6$ signifies alkyl, 3E-alkenyl, 4-alkenyl or on a trans-1,4-cyclohexylene ring also 1E-alkenyl or on a benzene ring also cyano, isothiocyanato, alkoxy, 2E-alkenyloxy or 3-alkenyloxy; $R^8$ denotes alkyl, 1E-alkenyl, 3E-alkenyl or 4-alkenyl; $Z^4$ and $Z^5$ each represent a single bond or ethylene, whereby aromatic rings are joined only by a single bond; $R^9$ signifies cyano, alkyl, 1E-alkenyl, 3E-alkenyl, 4-alkenyl, alkoxy, 2E-alkenyloxy, 3-alkenyloxy, alkoxymethyl or (2E-alkenyl)oxymethyl; $R^{10}$ denotes hydrogen, fluorine or chlorine; $R^{11}$ signifies fluorine, chlorine or cyano; $R^{12}$ represents alkyl, 1E-alkenyl, 3E-alkenyl or 4-alkenyl; $R^{13}$ signifies hydrogen or fluorine; and $R^{14}$ denotes fluorine or chlorine.

The above term "saturated ring" embraces trans-1,4-cyclohexylene and trans-1,3-dioxane-2,5-diyl. Residues $R^4$ to $R^9$ and $R^{12}$ each preferably have a maximum of 12 carbon atoms, particularly a maximum of 7 carbon atoms. Straight-chain residues are generally preferred.

The preparation of the liquid crystalline mixtures containing these newly disclosed compounds and the manufacture of electrooptical devices containing these mixtures can be accomplished by methods known in the art.

The invention is illustrated further by the following Examples. In the Examples, C signifies a crystalline phase, N signifies a nematic phase and I signifies the isotropic phase.

EXAMPLE 1 a) A suspension of 5.7 g of methoxymethyltriphenylphosphonium chloride in 100 ml of tert-butyl methyl ether is treated with 1.8 g of potassium tert-butylate at 0° C. while stirring and gassing with nitrogen. The suspension is stirred at 10° C. for a further 90 minutes, then treated dropwise at 0° C. within 10 minutes with a solution of 2.4 g of trans-4'-(4-chlorophenyl)-[1,1'-bicyclohexyl]-4-one in 50ml of tert.butyl methyl ether/methylene chloride (4:1) and stirred at room temperature for a further 2 hours. Then, the mixture is diluted with 100 ml of diethyl ether, washed three times with 100 ml of water each time and the organic phase is dried with anhydrous magnesium o sulphate, filtered and evaporated under reduced pressure. Purification of the residue (11 g) by chromatography on silica gel with n-hexane/ethyl acetate yields 2.5 g of trans-4-(4-chlorophenyl)-4'-(methoxymethylidene)-[1,1'-bicyclohexyl] as colourless crystals.

b) A solution of 2.6 trans-4-(4-chlorophenyl)-4'-(methoxymethylidene)-[1,1'-bicyclohexyl], 1.1 g of 2-(3-butenyl)-propane-1,3-diol and 0.1 g of p-toluenesulphonic acid in 80 ml of toluene is heated slowly to 120° C. (bath temperature) and about one third of the volume of toluene is distilled off. Thereafter, the reaction mixture is heated at reflux temperature, cooled after 15 hours and poured into a 5% solution of aqueous sodium bicarbonate. The aqueous mixture is treated with about 100 ml of diethyl ether and the separated organic phase is again washed with sodium bicarbonate solution, dried over anhydrous magnesium sulphate and evaporated under reduced pressure. The residue (3.4 g) is thereupon chromatographed on silica gel with toluene/ethyl acetate (1:1). Crystallization from n-hexane gives 1.93 g of trans-5-(3-butenyl)-2-{trans-4'-(4-chlorophenyl)-[1,1'-bicyclohexyl] -trans-4-yl}-1,3-dioxane as colourless crystals, m.p. (C-$S_B$) 94° C.,; $S_B$-N 189.3° C., cl.p. (N-I)>280° C.

The following compounds are manufactured in an analogous manner:

trans-5-(1E-Propenyl)-2-{trans-4'-(4-chlorophenyl)-[1,1'-bicyclohexyl]-trans-4-yl}-1,3-dioxane, m.p. (C-$S_B$) 117.9° C.; $S_B$-N 199° C.; cl.p. (N-I)>300° C.

trans-5-(1E-Propenyl)-2-{trans-4'-(4-chlorophenethyl)-[1,1'-bicyclohexyl] -trans-4-yl}-1,3-dioxane, m.p. (C-$S_B$) 128.6° C.; $S_B$-N 232° C.; cl.p. (N-I) 300° C.

trans-5-(3-Butenyl)-2-{trans-4'-(4-chlorophenethyl)-[1,1'-bicyclohexyl]-trans-4-yl}-1,3-dioxane, m.p. (C-$S_B$) 75.4° C.; $S_B$-N 240° C.; cl.p. (N-I) 262° C.

trans-5-(1E-Pentenyl)-2-{trans-4'-(4-fluorophenethyl)-[1,1'-bicyclohexyl] -trans-4-yl}-1,3-dioxane, m.p. (C-$S_B$) about 86.8° C.; $S_B$-N 269° C., cl.p. (N-I) 278° C.

trans-5-(4-Pentenyl)-2-{trans-4'-(4-fluorophenethyl)-[1,1'-bicyclohexyl]-trans-4-yl}-1,3-dioxane, m.p. (C-$S_B$) about 40° C.; cl.p. ($S_B$-I) 235° C.

trans-5-(4-Pentenyl)-2-[2-{trans-4'-(4-fluorophenethyl)-1,1' -bicyclohexyl]-trans-4-yl}-ethyl]-1,3-dioxane, m.p. (C-$S_B$) 79° C.; cl.p. ($S_B$-I) 223° C.

EXAMPLE 2 a) 0.1 ml of a solution of about 10 μl of dibromoethane in 1 ml of tetrahydrofuran is added to 33 mg of magnesium shavings in 0.5 ml of dry tetrahydrofuran. Then, a solution of 420 mg of 4-chloro-1-{4-trans-(1,4-dioxa-8-spiro[4,5]decyl)-cyclohexyl}-benzene in 1 ml of tetrahydrofuran and 2 ml of dry toluene are added and the reaction mixture is heated to 100° C. (oil bath temperature). After 24 hours the mixture is cooled to –70° C., 0.415 g of trimethylborate are added and the mixture is warmed slowly to room temperature. Then, 1 ml of 1N hydrochloric acid is added, the mixture is stirred for 30 minutes, thereupon partitioned between diethyl ether and water and the ether phase is washed twice with 1N sodium hydroxide solution. A suspension thereby forms in the ether phase. This is again washed with 1N hydrochloric acid and then several times with water, dried over anhydrous magnesium sulphate and evaporated under reduced pressure. The residue gives partially hydrolyzed 4-[trans-4-(1,4 -dioxa-8-spiro[4,5] decyl)-cyclohexyl]-phenylboric acid.

b) 210 mg of 4-[trans-4-(1,4-dioxa-8-spiro[4,5]decyl)-cyclohexyl]-phenylboric acid are dissolved in 2 ml of toluene and 0.8 ml of ethanol while warming. Then, 112 mg of 1-bromo-3,4-difluorobenzene and 23 mg of tetrakis(triphenylphosphine)-palladium (0) and 2 ml of saturated sodium carbonate solution are added. Thereupon, the mixture is heated at 80° C. (bath temperature) for 15 hours and stirred well. Then, it is cooled, partitioned between diethyl ether and water, the ether phase is evaporated and the residue is taken up in 5 ml of toluene/formic acid (1:1). This solution is stirred at 60° C. for 2 hours, then cooled, diluted with diethyl ether, washed several times with water and then with saturated sodium bicarbonate solution, dried over anhydrous magnesium sulphate and evaporated. Chromatography of the residue on silica gel with ethyl acetate/petroleum ether gives trans-4'-(3'-4'-difluoro-4-biphenylyl)-[1,1'-bicyclohexyl]-4-one.

c) A suspension of 5.707 g of dry (methoxymethyl)triphenylphosphonium chloride in 35 ml of tert.butyl methyl ether, gassed with nitrogen, is treated with 1.953 g of potassium tert.butylate at –15° C. while stirring, stirred for 30minutes and then warmed to –5° C. 4.1 g of trans-4'-(3'-4'-difluoro-4-biphenylyl)-[1,1'-bicyclohexyl]-4-one in 20ml of absolute tetrahydrofuran and 10 ml of tert.butyl methyl ether are added dropwise to the orange suspension within 10minutes, the cooling bath is removed, the reaction mixture is stirred at room temperature for 1.5 hours, diluted with 50 ml of n-hexane, filtered and the filter residue is washed with n-hexane. After purification by chromatography on 120 g of silica gel at a pressure of 0.5 bar with methylene chloride the product gives 4-{4'-(methoxymethylidene)-[1,1' -bicyclohexyl]-trans-4-yl}-3',4'-difluorobiphenyl.

d) A mixture of 4.5 g of 4-{4'-(methoxymethylidene)-[1, 1'-bicyclohexyl]-trans-4-yl}-3',4'-difluorobiphenyl in 18 ml of tertrahydrofuran and 4.5 ml of 2N hydrochloric acid is heated to boiling for 30 minutes while gassing with nitrogen, cooled, treated with 150 ml of water and extracted twice with 100 ml of methylene chloride each time. The organic phases are combined, washed with 100 ml of 10% sodium chloride solution, dried over anhydrous sodium sulphate and evaporated under reduced pressure. This gives a cis/trans mixture of 4-{4-(formyl)-[1,1'-bicyclohexyl]-trans-4-yl}-3',4'-difluorobiphenyl, which is dissolved in 80 ml of methanol and 8 ml of methylene chloride and stirred for 30minutes under nitrogen with 3 drops of triethylamine and 1.6 ml of 20% sodium hydroxide solution (g/g). The solution is treated with 150 ml of water and extracted twice with 100 ml of methylene chloride each time. The organic phase is washed with 100 ml of 10% sodium chloride solution, dried over anhydrous sodium sulphate and, after evaporation and after purification by chromatography on 120 g of silica gel at a pressure of 0.5 bar with n-hexane/ethyl acetate 99:1) and subsequent crystallization from methylene chloride/hexane at 0 C., gives pure 4-{trans-4'-(formyl)-[bicyclohexyl]-trans-4-yl}-3',4' -difluorobiphenyl.

e) 2.65 g ethyltriphenylphosphonium bromide are suspended in 40 ml of tert.butyl methyl ether while gassing with argon. The suspension is treated at room temperature with 797 mg of potassium tert.butylate and stirred for 1 hour. Subsequently, the mixture is cooled to 0° C., treated dropwise within 3 minutes with a solution of 2.5 g of 4-{trans-4'-(formyl)-[bicyclohexyl]-trans-4-yl}-3', 4'-difluorobiphenyl in 15 ml of tert.butyl methyl ether and then left to warm to room temperature while stirring slowly. After 2 hours the pale yellow suspension is partitioned in diethyl ether/water. The aqueous phase is separated and extracted three times with diethyl ether. The organic phases are washed twice with water, dried over anhydrous magnesium sulphate, filtered and evaporated under reduced pressure. Purification by chromatography on silica gel with ethyl acetate/ petroleum ether gives 4-{trans-4'-(1-propenyl)- [bicyclohexyl]-trans-4-yl}-3',4'-difluorobiphenyl as a Z/E mixture.

f) 2 g of 4-{trans-4'-(1-propenyl)-[bicyclohexyl]-trans-4-yl} -3',4'-difluorobiphenyl are treated with 6 ml of toluene, 0.11 g of sodium benzenesulphinate and 1 ml of 1N hydrochloric acid while gassing with nitrogen. The mixture is stirred at 50° C. for 15 hours, then poured into 100 ml of dilute sodium bicarbonate solution and extracted three times with 50 ml of diethyl ether each time. The combined organic phases are washed with 100 ml of dilute sodium carbonate solution and with 100 ml of water, dried over anhydrous magnesium sulphate, filtered and evaporated under reduced pressure. The residue is purified by chromatography on silica gel impregnated with silver nitrate using diethyl ether/n-hexane (1:9). Recrystallization of the resulting product from diethyl ether/methanol gives pure 4 -{trans-4-(1E-propenyl)-[1,1'-bicyclohexyl]- trans-4-yl}-3',4'-difluorobiphenyl, m.p. 118.8° C.; cl.p. (N-I) 332.5° C.

The following compounds were manufactured in an analogous manner:
4-{trans-4-Vinyl-[1,1'-bicyclohexyl]-trans-4-yl}-3',4'-difluorobiphenyl, m.p. (C-N) 98.1° C.; cl.p. (N-I)>287° C.;
4-{trans-4-(1E-propenyl)-[1,1'-bicyclohexyl]-trans-4-yl}- 4'-chlorobiphenyl, m.p. (C-N) 170° C., cl.p. (N-I)>450° C.;
4-[trans-4-(3-butenyl)cyclohexyl]-4"-fluoro-p-terphenyl, m.p. (C-N) 189.7° C., cl.p. (N-I) 327.5° C.

EXAMPLE 3 a) 780 mg of sodium borohydride are dissolved in 30 ml of methanol/diethyl ether (9:1). This solution is treated dropwise at 0° C. within 10 minutes with a solution of 10.5 g of 3-{trans-4'-(3',4'-difluoro-4 -biphenylyl)-[1, 1'-bicyclohexyl]-trans-4-yl}-propanol in 40ml of methanol/diethyl ether (9:1) and stirred further at 0° C. After 1.5 hours the reaction mixture is again treated with 200 mg of sodium borohydride and stirred at 0° C. for a further 3.5 hours. Subsequently, the reaction mixture is acidified (pH about 2) with 20 ml of dilute hydrochloric acid and extracted three times with methylene chloride. The organic phases are washed with dilute hydrochloric acid and twice with water, dried over anhydrous magnesium sulphate and evaporated under reduced pressure. The crude product is purified by chromatography on silica gel. There is thus obtained 4-{trans-4'-(3-hydroxypropyl)-[1,1' -bicyclohexyl]- trans-4-yl}-3',4'-difluororbiphenyl.

b) 1.2 g of sodium hydride (as a 50% suspension in oil) are suspended in 20 ml of tetrahydrofuran and the suspension is treated dropwise at room temperature within 5 minutes with a solution of 6.5 g of 4-{trans- 4'-(3-hydroxypropyl)-[1,1'-bicyclohexyl]-trans-4-yl}- 3',4'-difluororbiphenyl in 40ml of tetrahydrofuran. The reaction mixture is stirred at room temperature for a further 5 minutes, then treated with 3.75 ml of propyl iodide and stirred under reflux (bath temperature 70° C.) for a further 2 hours. Subsequently, the white suspension is partitioned in diethyl ether/water and extracted three times with diethyl ether. The organic phases are washed twice with water, dried over anhydrous magnesium sulphate, filtered and evaporated under reduced pressure. The crude product is purified by chromatography on silica gel with ethyl acetate/ petroleum ether and recrystallized several times from methanol/diethyl ether. There is thus obtained 4-{trans- 4'-(3 -methoxypropyl)-[1,1'-bicyclohexyl]-trans-4-yl}- 3',4'-difluorobiphenyl.

EXAMPLE 4

A mixture of 3.7 g of trans-4'-(1E-propenyl)-[1,1'-bicyclohexyl]-trans-4-yl malonaldehyde tetramethyl acetal (produced by reduction of trans-4'-(1E-propenyl)-[1,1'-bicyclohexyl]-trans-4-carbonitrile with diisobutylaluminium hydride, Wittig reaction of the resulting in aldehyde with (methoxymethyl)triphenylphosphonium chloride/potassium tert.butylate and boron trifluoride-catalyzed reaction of the methoxyvinyl compound with trimethyl orthoformate), 0.07 g of p-toluenesulphonic acid monohydrate and 0.2 ml of water is stirred for 2 hours at a bath temperature of 100° C. The reaction mixture is then stirred with 0.3 g of sodium bicarbonate for 5 minutes without the bath, filtered and the residue is rinsed with methanol. The solution is treated with a solution of 1.9 g of 4-chlorobenzamidine hydrochloride in 35 ml of methanol and then with a sodium methylate solution pre-prepared from 0.42 g of sodium and 10 ml of methanol. The mixture is stirred at room temperature for about 16 hours and the resulting suspension is adjusted to pH 5 by the addition of concentrated hydrochloric acid and suction filtered. The thus-obtained crude 5-{trans-4'-(1E-propenyl)-[ 1,1'-bicyclohexyl]-trans-4-yl}-2-(4-chlorophenyl)-pyrimidine is washed with a small amount of methanol, dried and recrystallized from ethyl acetate.

EXAMPLE 5

Mixtures of a "basic mixture" (BM) of the following composition and in each case a compound of formula I were produced in order to investigate the properties of the compounds of formula I in mixtures:

| Basic Mixture (BM) | |
| --- | --- |
| Compound | Weight percent |
| 5-(trans-4-Butylcyclohexyl)-2-pyrimidine- carbonitrile | 4.12 |
| p-(trans-4-Vinylcyclohexyl)-benzonitrile | 8.25 |
| p-[trans-4-(1E-Propenyl)-cyclohexyl]-benzonitrile | 8.25 |
| p-[trans-4-(3-Butenyl)-cyclohexyl]-benzonitrile | 6.18 |
| p-[trans-4-(3E-Pentenyl)-cyclohexyl]-benzonitrile | 7.22 |
| [trans-4'-(3-Butenyl)-[1,1'-bicyclohexyl]-trans-4-yl]- carboxylic acid (p-fluorophenyl) ester | 8.25 |
| 1-[2-(trans-4-Butyl-cyclohexyl)-ethyl]-4-[trans-4- (4-pentenyl)-cyclohexyl]-benzene | 6.18 |
| 4-Ethyl-4'-[trans-4-(3E-pentenyl)-cyclohexyl]- biphenyl | 4.12 |
| 1-[2-(trans-4-Butyl-cyclohexyl)-ethyl]-4-(trans-4- pentyl-cyclohexyl)-benzene | 8.25 |
| trans-4-Ethoxy-trans-4'-(3-butenyl)-1,1'-bicyclo- hexyl | 9.28 |
| trans-4-Ethoxy-trans-4'-(3E-pentenyl)-1,1'- bicyclohexyl | 8.25 |
| trans-4-Methoxy-trans-4'-(3E-pentenyl)-1,1'- bicyclohexyl | 8.25 |
| trans-4-Propylcyclohexanecarboxylic acid {p-[trans- 4-(3-pentenyl)-cyclohexyl]-phenyl} ester | 7.22 |

-continued

Basic Mixture (BM)

| Compound | Weight percent |
|---|---|
| 4-[2-(trans-4-Propylcyclohexyl)-ethyl]-4'-(trans-4-pentyl-cyclohexyl)-biphenyl | 4.12 |
| trans-4-Ethoxy-trans-4'-(4-pentenyl)-1,1'-bicyclohexyl | 2.06 |

The first mixture with a compound of formula I ("Mixture 1") consisted of 97 wt. % of the BM and 3 wt. % of trans-5-(3-butenyl)-2-{trans-4'-(4-chlorophenyl)-[1,1'-bicyclohexyl]-trans-4-yl}-1,3-dioxane.

The second ("Mixture 2") consisted of 97 wt. % of the BM and 3 wt. % of trans-5-(1E-propenyl)-2-{trans-4'-(4-chlorophenyl)-[1,1'-bicyclohexyl]-trans-4-yl}-1,3-dioxane.

The potentials in volt (V) for 10% transmission ($V_{10}$) and 50% transmission ($V_{50}$) and the response times in milliseconds (switching-on time $t_{on}$ and, respectively, switching-off time $t_{off}$) were measured in a TN cell (low bias tilt) having a plate separation of 6μm at 22° C., −20° C. and −30° C.; the 2.5-fold value of the threshold potential was chosen as the operating voltage. The melting point ($T_m$) and the clearing point ($T_c$) of the respective mixture were also measured.

The results of the investigation are compiled in the following Table:

| Properties | BM | Mixture 1 | Mixture 2 |
|---|---|---|---|
| $V_{10}$ (V) | 2.153 | 2.150 | 2.145 |
| $V_{50}$ (V) | 2.526 | 2.534 | 2.535 |
| $t_{on}$ (ms) at 22° C. | 14.3 | 15.1 | 14.4 |
| $t_{on}$ (ms) at −20° C. | 177 | 174 | 185 |
| $t_{on}$ (ms) at −30° C. | 493 | 469 | 529 |
| $t_{off}$ (ms) at 22° C. | 24.1 | 25.3 | 23.8 |
| $t_{off}$ (ms) at −20° C. | 319 | 336 | 345 |
| $t_{off}$ (ms) at −30° C. | 915 | 874 | 973 |
| $T_m$ (°C.) | <−25 | <−25 | <−25 |
| $T_c$ (°C.) | 91.2 | 95.0 | 96.8 |

From the results tabulated above it will be seen that the novel compounds I considerably increase the clearing point $T_c$ even in low concentrations, but do not lead to a simultaneous increase in the threshold potential $V_{10}$ and do not lead (or lead only immaterially) to a lengthening of the switching times.

We claim:

1. A compound of the formula

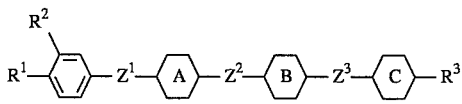

wherein rings A and B, each independently, are selected from the group consisting of trans-1,4-cyclohexylene, 1,4-phenylene, which is unsubstituted, monosubstituted or disubstituted, the substituent selected from the group consisting of halogen, cyano and methyl, pyridine-2,5-diyl, and pyrimidine-2,5-diyl, ring C is trans-1,4-cyclohexylene or trans-1,3-dioxane-2,5-diyl, $Z^1$ and $Z^2$, each independently, is a single bond, or where linked with at least one saturated ring, a single bond or ethylene, $Z^3$ is a single bond or ethylene, $R^1$ is fluorine or chlorine, $R^2$ is hydrogen or fluorine and $R^3$ is selected from the group consisting of $C_{2-12}$-1E-alkenyl, $C_{4-12}$-3E-alkenyl, and $C_{5-12}$-4-alkenyl;

with the provisos that (a) where ring B is (hetero)aromatic, ring A is not simultaneously trans-1,4-cyclohexylene, (b) a maximum of two trans-1,4-cyclohexylene groups each linked with a single bond are present, (c) a maximum of one of rings A and B is pyridine-2,5-diyl or pyrimidine-2,5-diyl and (d) where simultaneously $R^1$ is fluorine and $R^3$ is $C_{2-12}$-1E-alkenyl or $C_{4-12}$-3E-alkenyl, $R^2$ is fluorine.

2. A compound according to claim 1, wherein ring A is trans-1,4-cyclohexylene or unsubstituted 1,4-phenylene.

3. A compound according to claim 1, wherein ring B is trans-1,4-cyclohexylene.

4. A compound according to claim 2, wherein ring B is trans-1,4-cyclohexylene.

5. A compound according to claim 1, wherein $Z^1$ is a single bond and $Z^2$ and $Z^3$ are not both ethylene.

6. A compound according to claim 1, wherein $R^3$ is selected from the group consisting of vinyl, 1E-propenyl, 1E- or 3-butenyl, 1E-, 3E- or 4-pentenyl, 1E- or 3E-hexenyl and 1E- or 3E-heptenyl.

7. A compound according to claim 1, wherein ring A and B each are trans-1,4-cyclohexylene; and ring C is trans-1,3-dioxane.

8. A compound according to claim 1, wherein ring A is 1,4-phenylene; and rings B and C each are trans-1,4-cyclohexylene.

9. A liquid crystalline mixture comprising at least two components, wherein at least one component is a compound of the formula

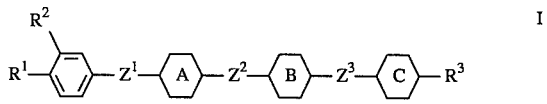

wherein rings A and B, each independently, are selected from the group consisting of trans-1,4-cyclohexylene, 1,4-phenylene, which is unsubstituted, monosubstituted or disubstituted, the substituent selected from the group consisting of halogen, cyano and methyl, pyridine-2,5-diyl, and pyrimidine-2,5-diyl, ring C is trans-1,4-cyclohexylene or trans-1,3-dioxane-2,5-diyl, $Z^1$ and $Z^2$, each independently, is a single bond, or where linked with at least one saturated ring, a single bond or ethylene also ethylene, $Z^3$ is a single bond or ethylene, $R^1$ is fluorine or chlorine, $R^2$ is hydrogen or fluorine and $R^3$ is selected from the group consisting of $C_{2-12}$-1E-alkenyl, $C_{4-12}$-3E-alkenyl, and $C_{5-12}$-4-alkenyl or;

with the provisos that (a) where ring B is (hetero)aromatic, ring A is not simultaneously trans-1,4-cyclohexylene, (b) a maximum of two trans-1,4-cyclohexylene groups each linked with a single bond are present, (c) a maximum of one of rings A and B is pyridine-2,5-diyl or pyrimidine-2,5-diyl and (d) where simultaneously $R^1$ is fluorine and $R^3$ is $C_{2-12}$-1E-alkenyl or $C_{4-12}$-3E-alkenyl, $R^2$ is fluorine.

10. A liquid crystalline mixture according to claim 7, which comprises from about 2 wt. % to about 30 wt. % of compounds of formula I.

11. A liquid crystalline mixture according to claim 7, comprising at least one compound of formula I and at least one one compound selected from the group of compounds of the formulae

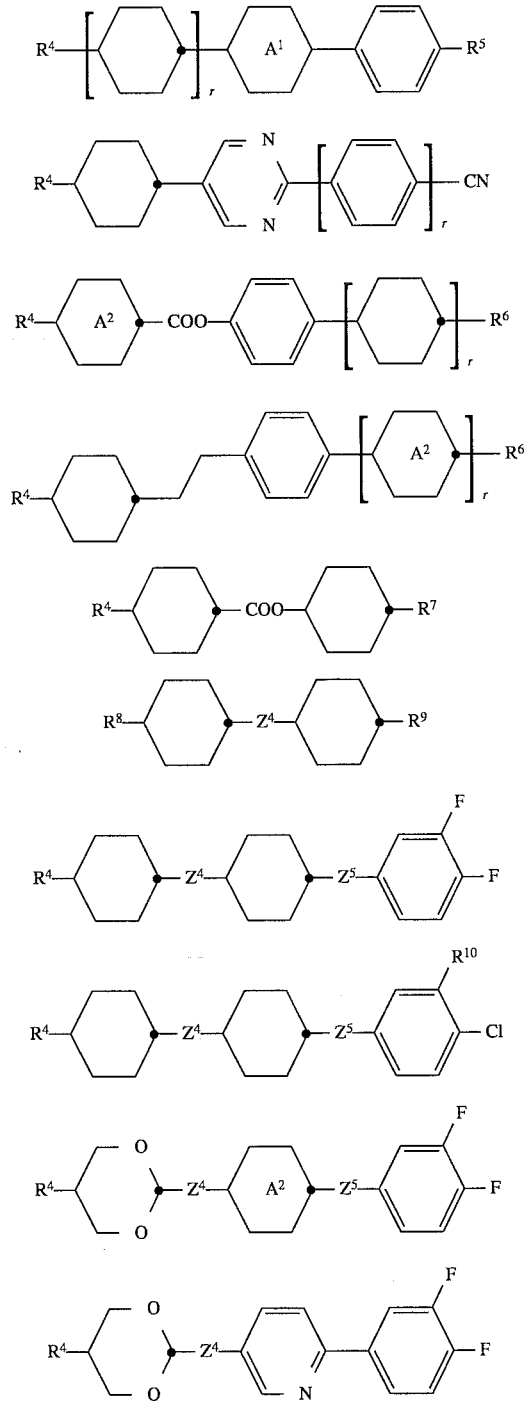

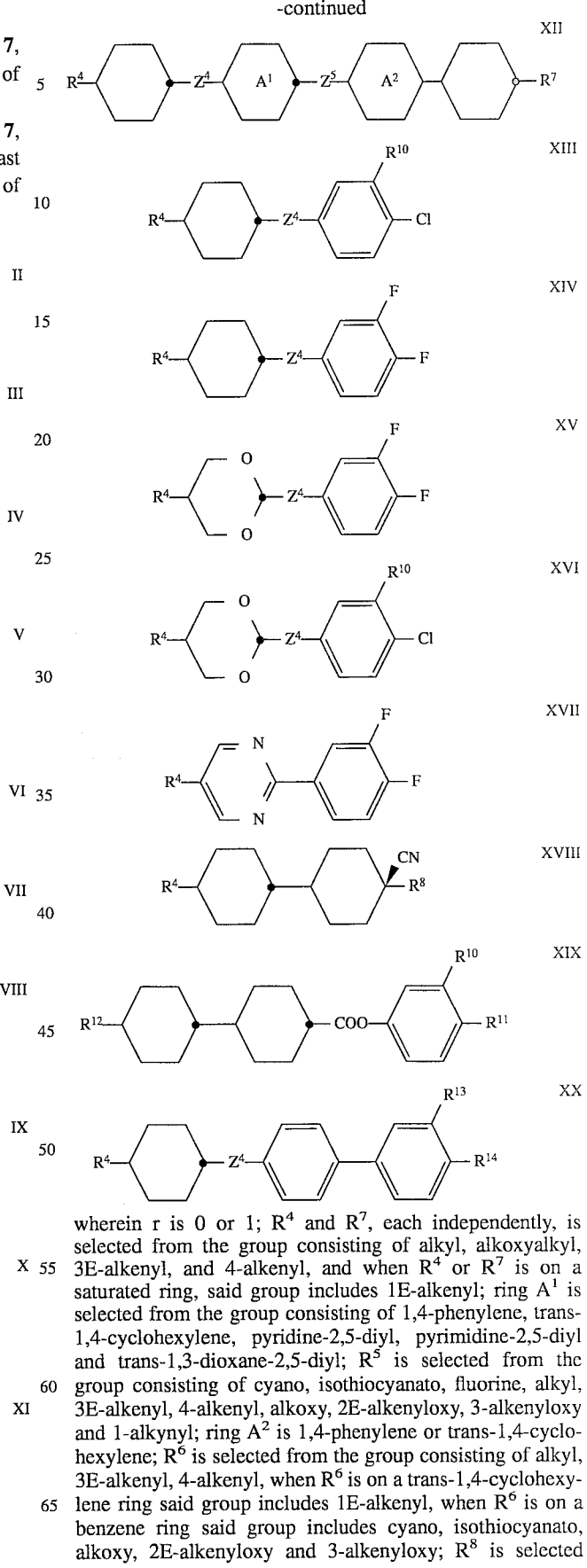

wherein r is 0 or 1; $R^4$ and $R^7$, each independently, is selected from the group consisting of alkyl, alkoxyalkyl, 3E-alkenyl, and 4-alkenyl, and when $R^4$ or $R^7$ is on a saturated ring, said group includes 1E-alkenyl; ring $A^1$ is selected from the group consisting of 1,4-phenylene, trans-1,4-cyclohexylene, pyridine-2,5-diyl, pyrimidine-2,5-diyl and trans-1,3-dioxane-2,5-diyl; $R^5$ is selected from the group consisting of cyano, isothiocyanato, fluorine, alkyl, 3E-alkenyl, 4-alkenyl, alkoxy, 2E-alkenyloxy, 3-alkenyloxy and 1-alkynyl; ring $A^2$ is 1,4-phenylene or trans-1,4-cyclohexylene; $R^6$ is selected from the group consisting of alkyl, 3E-alkenyl, 4-alkenyl, when $R^6$ is on a trans-1,4-cyclohexylene ring said group includes 1E-alkenyl, when $R^6$ is on a benzene ring said group includes cyano, isothiocyanato, alkoxy, 2E-alkenyloxy and 3-alkenyloxy; $R^8$ is selected from the group consisting of alkyl, 1E-alkenyl, 3E-alkenyl and 4-alkenyl; $Z^4$ and $Z^5$, each independently, represent a single bond or ethylene, whereby aromatic rings are joined only by a single bond; $R^9$ is selected from the group consisting of cyano, alkyl, 1E-alkenyl, 3E-alkenyl, 4-alkenyl, alkoxy, 2E-alkenyloxy, 3-alkenyloxy, alkoxymethyl and (2E-alkenyl)oxymethyl; $R^{10}$ is either hydrogen, fluorine or chlorine; $R^{11}$ is fluorine, chlorine or cyano; $R^{12}$ is selected from the group consisting of alkyl, 1E-alkenyl, 3E-alkenyl and 4-alkenyl; $R^{13}$ is hydrogen or fluorine; and $R^{14}$ is fluorine or chlorine.

12. A compound according to claim 1 of the formula

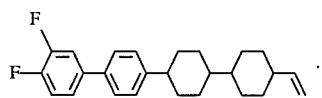

13. The liquid crystalline mixture according to claim 9, wherein at least one component is a compound of the formula

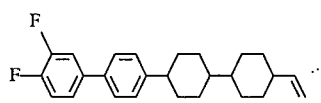

* * * * *

UNITED STATES PATENT AND TRADEMARK OFFICE
CERTIFICATE OF CORRECTION

PATENT NO. : 5,478,497
DATED : December 26, 1995
INVENTOR(S) : Richard Buchecker et al.

It is certified that error appears in the above-indentified patent and that said Letters Patent is hereby corrected as shown below:

In claim 9, column 34, line 59, delete last word "or".

Signed and Sealed this

Twenty-eighth Day of May, 1996

Attest:

BRUCE LEHMAN

*Attesting Officer*      *Commissioner of Patents and Trademarks*